(12) United States Patent
Tanaka et al.

(10) Patent No.: US 7,039,227 B2
(45) Date of Patent: May 2, 2006

(54) PET DEVICE AND IMAGE GENERATING METHOD FOR PET DEVICE

(75) Inventors: Eiichi Tanaka, Hamamatsu (JP); Takaji Yamashita, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 700 days.

(21) Appl. No.: 10/276,221

(22) PCT Filed: May 23, 2001

(86) PCT No.: PCT/JP01/04324

§ 371 (c)(1),
(2), (4) Date: Nov. 14, 2002

(87) PCT Pub. No.: WO01/90780

PCT Pub. Date: Nov. 29, 2001

(65) Prior Publication Data

US 2003/0108229 A1 Jun. 12, 2003

(30) Foreign Application Priority Data

May 24, 2000 (JP) .............................. 2000-153580

(51) Int. Cl.
*G06K 9/00* (2006.01)
*G01T 1/164* (2006.01)

(52) U.S. Cl. .................................. 382/131; 250/363.03

(58) Field of Classification Search ........ 382/128–131; 250/363.03

See application file for complete search history.

(56) References Cited

U.S. PATENT DOCUMENTS 4,352,018 A * 9/1982 Tanaka et al. ......... 250/363.03

(Continued)

FOREIGN PATENT DOCUMENTS

JP 7-198853 8/1995

(Continued)

OTHER PUBLICATIONS

Turkington, T.G. et al, "Scatter Correction for Two-Camera Coincidence Imaging," Nuclear Science Symposium, 1997, IEEE Albuquerque, NM, Nov. 9-15, 1997, New York, NY, vol. 2, Nov. 9, 1997, pps. 1198-1202.

Primary Examiner—Kanjibhai Patel
Assistant Examiner—ONeal R. Mistry
(74) Attorney, Agent, or Firm—Drinker Biddle & Reath LLP

(57) ABSTRACT

A PET apparatus is provided, which ensures excellent quantitativeness by properly correcting the influence of scattered radiation while improving the resolution of a reconstructed image and keeping good photon pair detection sensitivity. A determining section 52 determines whether a straight line connecting the light-receiving surfaces 15b of a pair of photon detectors 15a which have simultaneously detected a photon pair crosses any one of slice collimators $21_n$. When it is determined that the straight line crosses none of the slice collimators $21_n$, the corresponding coincidence counting information is accumulated by a first coincidence counting information storage section 53 to generate a signal sinogram. When it is determined that the straight line crosses one of the slice collimators $21_n$, the corresponding coincidence counting information is accumulated by a second coincidence counting information storage section 54 to generate a scatter sinogram. An image reconstructing section 60 corrects the influence of scattered components on the signal sinogram on the basis of the scattered sinogram, and reconstructs an image on the basis of the corrected signal sinogram.

12 Claims, 12 Drawing Sheets

U.S. PATENT DOCUMENTS

| | | | |
|---|---|---|---|
| 5,023,894 A * | 6/1991 | Yamashita et al. | 378/4 |
| 5,291,021 A * | 3/1994 | Tanaka et al. | 250/363.03 |
| 5,331,552 A * | 7/1994 | Lloyd et al. | 378/15 |
| 5,471,061 A * | 11/1995 | Moyers et al. | 250/363.03 |
| 6,040,580 A * | 3/2000 | Watson et al. | 250/363.03 |
| 6,175,116 B1 * | 1/2001 | Gagnon et al. | 250/363.03 |
| 6,211,523 B1 * | 4/2001 | Gagnon | 250/363.04 |
| 6,249,003 B1 * | 6/2001 | Culp | 250/363.04 |
| 2003/0021375 A1 * | 1/2003 | Jones et al. | 378/51 |
| 2004/0004191 A1 * | 1/2004 | Worstell et al | 250/394 |

FOREIGN PATENT DOCUMENTS

| | | |
|---|---|---|
| JP | 7-318654 | 12/1995 |
| JP | 8-313636 | 11/1996 |
| JP | 9-33659 | 2/1997 |
| JP | 10-142338 | 5/1998 |
| JP | 11-101874 | 4/1999 |
| JP | 11-101875 | 4/1999 |
| JP | 2000-28727 | 1/2000 |

* cited by examiner

Z-AXIS (CAX)

PET DEVICE AND IMAGE GENERATING METHOD FOR PET DEVICE

TECHNICAL FIELD

The present invention relates to a PET apparatus and an image generating method for the PET apparatus which can image the behavior of a substance marked by a positron emission isotope (RI radiation source).

BACKGROUND ART

A PET (Positron Emission Tomography) apparatus is an apparatus which can image the behavior of a trace substance in an object (living body) to be examined by detecting a pair of 511 keV photons (gamma rays) which fly in opposite directions upon electron-positron pair annihilation in the object irradiated with RI radiation. The PET apparatus includes a detecting section having many small photon detectors arrayed around a measurement space in which an object to be examined is placed. This apparatus detects a photon pair generated upon electron-positron pair annihilation by coincidence counting, accumulates the coincidence counting information, and reconstructs an image representing the spatial distribution of occurrence frequencies of photon pairs in the measurement space on the basis of these many pieces of accumulated coincidence counting information. This PET apparatus serves an important role in the field of nuclear medicine and the like. For example, biofunctions and the high-order brain functions can be studied by using this apparatus. Such PET apparatuses are roughly classified into two-dimensional PET apparatuses and three-dimensional PET apparatuses.

FIG. 11 is a view for explaining the arrangement of the detecting section of a two-dimensional PET apparatus. FIG. 11 shows an example of an arrangement including seven detector rings, and is a sectional view of the detecting section taken along a plane including the central axis. A detecting section 10 of the two-dimensional PET apparatus has detector rings $R_1$ to $R_7$ stacked between a shield collimator 11 and a shield collimator 12. Each of the detector rings $R_1$ to $R_7$ has a plurality of photon detectors arranged in the form of a ring on a plane perpendicular to the central axis. Each photon detector is a scintillation detector formed from a combination of a scintillator such as BGO ($Bi_4Ge_3O_{12}$) and a photomultiplier. This detector detects photons flying from a measurement space including the central axis. The two-dimensional PET apparatus has slice collimators $S_1$ to $S_6$ inside the detecting section 10. These slice collimators $S_1$ to $S_6$ are ring-like members each of which is placed between adjacent detector rings in a direction parallel to the central axis. Each slice collimator is made of a material having a larger atomic number and larger specific gravity (e.g., lead or tungsten) and has a collimating function of shielding obliquely incident photons (gamma rays).

The detecting section 10 of the two-dimensional PET apparatus having the above arrangement can perform coincidence counting of only a photon pair flying from the nearly 90° direction with respect to the central axis owing to the collimating function of the slice collimators $S_1$ to $S_6$. That is, the coincidence counting information, i.e., two-dimensional projection data, accumulated by the detecting section 10 of the two-dimensional PET apparatus is limited to that obtained by a pair of photon detectors included in a single detector ring or detector rings which are adjacent to each other (or very close to each other). The two-dimensional PET apparatus can therefore efficiently remove scattered radiation produced when a photon pair generated outside the measurement space is scattered. In addition, this apparatus can easily perform absorption correction and sensitivity correction with respect to two-dimensional projection data, and hence can obtain a reconstructed image with good quantitativeness.

FIG. 12 is a view for explaining the arrangement of the detecting section of the three-dimensional PET apparatus. FIG. 12 is also a sectional view of the detecting section taken along a plane including the central axis. The arrangement of the detecting section 10 of the three-dimensional PET apparatus is the same as that of the two-dimensional PET apparatus except that the three-dimensional PET apparatus has no slice collimators. The detecting section 10 of the three-dimensional PET apparatus having this arrangement has a wide solid angle and can perform coincidence counting of a photon pair flying from a wide range as compared with the two-dimensional PET apparatus. That is, as the coincidence counting information, i.e., three-dimensional projection data, obtained and accumulated by the detecting section 10 of the three-dimensional PET apparatus, data obtained by a pair of photon detectors included in an arbitrary detector ring can be used. Three-dimensional PET apparatus can therefore perform coincidence counting of a photon pair with sensitivity five to ten times higher than that of the two-dimensional PET apparatus. As compared with the two-dimensional PET apparatus, however, the three-dimensional PET apparatus has difficulty in accurately removing the influence of scattered radiation, and hence the quantitativeness of a reconstructed image is poor.

As described above, as compared with the three-dimensional PET apparatus, the two-dimensional PET apparatus having slice collimators has low photon pair detection sensitivity but can efficiently remove scattered radiation and easily perform absorption correction and sensitivity correction. The two-dimensional PET apparatus therefore has the merit of obtaining a reconstructed image with excellent quantitativeness.

DISCLOSURE OF THE INVENTION

The above PET apparatuses, however, have the following problems. Both the two-dimensional PET apparatus and the three-dimensional PET apparatus are required to improve the resolution of an image. In order to improve the resolution, it is indispensable to reduce the size of each photon detector.

In the case of the two-dimensional PET apparatus, however, the intervals between the respective slice collimators decrease with a reduction in the size of each photon detector, and hence the open area ratio decreases to result in a deterioration in photon pair detection sensitivity. In the two-dimensional PET apparatus, a reduction in open area ratio can be suppressed by thinning and shortening each slice collimator in accordance with a reduction in the size of each photon detector. This, however, decreases the effect of shielding photons (gamma rays), i.e., the collimating effect, and hence scattered radiation cannot be efficiently removed, resulting in a deterioration in the quantitativeness of a reconstructed image.

In the case of the three-dimensional PET apparatus, even if the size of each photon detector is reduced, since no slice collimator is used, no problem arises concerning a reduction in open area ratio or a decrease in photon pair detection sensitivity. As described above, however, since it is essentially difficult to eliminate the influence of scattered radiation in the three-dimensional PET apparatus, the quantitativeness of a reconstructed image is poor.

The present invention has been made to solve the above problems, and has as its object to provide a PET apparatus and an image generating method for the PET apparatus, which realize excellent quantitativeness by properly correcting the influence of scattered radiation while improving the resolution of a reconstructed image and keeping photon pair detection sensitivity high.

According to an aspect of the present invention, there is provided a PET apparatus characterized by comprising (1) a detecting section which includes a plurality of cylindrical detectors each formed by two-dimensionally arraying a plurality of photon detection elements, each of which detects a photon flying from a measurement space including a central axis, on a cylinder surrounding the central axis, the plurality of cylindrical detectors being arrayed in a direction parallel to the central axis, (2) a plurality of slice collimators which are alternately arranged with the cylindrical detectors at least between the measurement space and the detecting section in a direction parallel to the central axis, and pass only photons, of photons flying from the measurement space, which are substantially parallel to a predetermined plane perpendicular to the central axis toward the detecting section, (3) a determining section which determines, when a pair of photon detection elements included in the detecting section simultaneously detect a photon pair, whether a straight line connecting light-receiving surfaces of the pair of photon detection elements crosses any one of the plurality of slice collimators, (4) a first coincidence counting information accumulating section which accumulates coincidence counting information of the photon pair detected by the pair of photon detection elements when the determining section determines that the straight line crosses none of the plurality of slice collimators, (5) a second coincidence counting information accumulating section which accumulates coincidence counting information of the photon pair detected by the pair of photon detection elements when the determining section determines that the straight line crosses one of the plurality of slice collimators, and (6) an image reconstructing section which corrects an influence of a scattered component on the coincidence counting information accumulated by the first coincidence counting information accumulating section on the basis of the coincidence counting information accumulated by the second coincidence counting information accumulating section, and reconstructs an image representing a spatial distribution of occurrence frequencies of photon pairs in the measurement space on the basis of the corrected coincidence counting information.

According to the PET apparatus according to an aspect of the present invention, of 511 keV photon (gamma ray) pairs generated upon electron-positron pair annihilation in a measurement space, a photon pair that has reached the detecting section without being shielded by a plurality of slice collimators are simultaneously detected by a pair of photon detection elements included in the detecting section. The determining section determines whether a straight line connecting the light-receiving surfaces of the pair of photon detection elements that have simultaneously detected the photon pair crosses any one of the slice collimators. If the determining section determines that the straight line crosses none of the slice collimators, the coincidence counting information of the photon pair detected by the pair of photon detection elements is accumulated by the first coincidence counting information accumulating section. If the determining section determines that the straight line crosses one of the slice collimators, the coincidence counting information of the photon pair detected by the pair of photon detection elements is accumulated by the second coincidence counting information accumulating section. When a predetermined measurement period comes to an end, the first and first coincidence counting information accumulating sections stop accumulating coincidence counting information. The image reconstructing section corrects the influence of scattered components on a signal sinogram accumulated and generated by the first coincidence counting information accumulating section, on the basis of a scatter sinogram accumulated and generated by the first coincidence counting information accumulating section, and reconstructs an image representing the spatial distribution of occurrence frequencies of photon pairs in the measurement space on the basis of the corrected signal sinogram.

In the PET apparatus according to one aspect of the present invention, detection of coincidence counting information may be performed by a pair of photon detection elements in the same cylindrical detector included in the detecting section, a pair of photon detection elements respectively included in two adjacent cylindrical detectors depending on the sizes of each cylindrical detector and each slice collimator, or a pair of photon detection elements included in two separate cylindrical detectors. In other words, detection of coincidence counting information may be performed between two adjacent detector rings or between two separate detector rings as well as within the same detector ring (one layer of photon detection elements arrayed in the form of a ring in a direction parallel to the central axis). That is, the PET apparatus according to the present invention has an intermediate arrangement between a conventional two-dimensional PET apparatus and a conventional three-dimensional PET apparatus, and has sensitivity about several times higher than that of the conventional two-dimensional PET apparatus. The PET apparatus according to the present invention can therefore ensure good photon pair detection sensitivity and quantitativeness while improving the resolution of a reconstructed image.

In the PET apparatus according to one aspect of the present invention, in particular, the determining section determines whether a straight line connecting the light-receiving surfaces of a pair of photon detection elements which have simultaneously detected a photon pair crosses any one of the slice collimators. The first coincidence counting information accumulating section generates a signal sinogram on the basis of this determination result. The second coincidence counting information accumulating section generates a scatter sinogram. The image reconstructing section then corrects the influence of scattered components on the signal sinogram on the basis of the scatter sinogram, and reconstructs an image on the basis of the corrected signal sinogram. As described above, according to the present invention, scattered radiation is removed by a plurality of slice collimators, and the influence of scattered components on the signal sinogram is corrected on the basis of the scatter sinogram. This makes a reconstructed image have excellent quantitativeness.

In the PET apparatus according to one aspect of the present invention, each cylindrical detector is characterized by being formed by arraying two-dimensional position detectors, each for detecting the two-dimensional incident position of a photon on a light-receiving surface when the photon is incident on the light-receiving surface, on a predetermined plane in the form of a ring. This arrangement is suitable to improve the resolution of a reconstructed image by reducing the size of each photon detection element.

In addition, the PET apparatus according to one aspect of the present invention is characterized in that the apparatus further comprises moving means for moving the detecting section and the plurality of slice collimators together relative to an object to be examined which is placed in the measurement space in a direction parallel to the central axis, and the first and second coincidence counting information accumulating sections respectively acquire coincidence counting information during a period in which the detecting section and the plurality of slice collimators are moved relative to the object by the moving means, convert the coincidence counting information into information in a coordinate system fixed to the object, and accumulate the information. In this case, coincidence counting information is acquired during a period in which the detecting section and slice collimators are moved relative to the object in a direction parallel to the central axis by the moving means. The information is converted into information in a coordinate system fixed to the object and accumulated in the first coincidence counting information accumulating section or second coincidence counting information accumulating section. The image reconstructing section obtains a reconstructed image on the basis of the accumulated coincidence counting information (signal sinogram and scatter sinogram). With the above arrangement of the cylindrical detectors and slice collators, therefore, photon pairs can be detected with uniform sensitivity in the body axis direction of the object, and the quantitativeness of a reconstructed image can be made uniform.

A PET apparatus according to another aspect of the present invention comprises a plurality of photon detection elements which are arranged around a measurement space and detect one photon and the other photon which are produced upon electron-positron pair annihilation, a plurality of collimators which guide only the photon flying from a predetermined direction toward each of the plurality of photon detection elements, a determining section which determines, when detection of one photon by one of the plurality of photon detection elements and detection of the other photon by one of the plurality of photon detection elements are simultaneously done, whether a straight line connecting a light-receiving surface of the photon detection element which has detected one photon and a light-receiving surface of the photon detection element which has detected the other photon crosses any one of the plurality of collimators, a first coincidence counting information accumulating section which accumulates coincidence counting information of one photon and the other photon when the determining section determines that the straight line crosses none of the plurality of slice collimators, a second coincidence counting information accumulating section which accumulates coincidence counting information of one photon and the other photon when the determining section determines that the straight line crosses one of the plurality of slice collimators, and an image reconstructing section which corrects an influence of a scattered component on the coincidence counting information accumulated by the first coincidence counting information accumulating section on the basis of the coincidence counting information accumulated by the second coincidence counting information accumulating section, and reconstructs an image representing a spatial distribution of occurrence frequencies of a pair of one photon and the other photon in the measurement space on the basis of the corrected coincidence counting information.

The same as that applies to the PET apparatus according to another aspect of the present invention applies to the PET apparatus according to one aspect of the present invention.

According to still another aspect of the present invention, an image generating method for a PET apparatus including a plurality of photon detection elements which are arranged around a measurement space and detect one photon and the other photon which are produced upon electron-positron pair annihilation, and a plurality of collimators which guide only the photon flying from a predetermined direction toward each of the plurality of photon detection elements, comprises the determining step of determining, when detection of one photon by one of the plurality of photon detection elements and detection of the other photon by one of the plurality of photon detection elements are simultaneously done, whether a straight line connecting a light-receiving surface of the photon detection element which has detected one photon and a light-receiving surface of the photon detection element which has detected the other photon crosses any one of the plurality of collimators, the first coincidence counting information accumulating step of accumulating coincidence counting information of one photon and the other photon when it is determined in the determining step that that the straight line crosses none of the plurality of slice collimators, the second coincidence counting information accumulating step of accumulating coincidence counting information of one photon and the other photon when it is determined in the determining step that the straight line crosses one of the plurality of slice collimators, and the image reconstructing step of correcting an influence of a scattered component on the coincidence counting information accumulated in the first coincidence counting information accumulating step on the basis of the coincidence counting information accumulated in the second coincidence counting information accumulating step, and reconstructing an image representing a spatial distribution of occurrence frequencies of a pair of one photon and the other photon in the measurement space on the basis of the corrected coincidence counting information.

The same as that applies to the image generating method for the PET apparatus according to still another aspect of the present invention applies to the PET apparatus according to one aspect of the present invention.

BEST MODE FOR CARRYING OUT THE INVENTION

Figure 1:
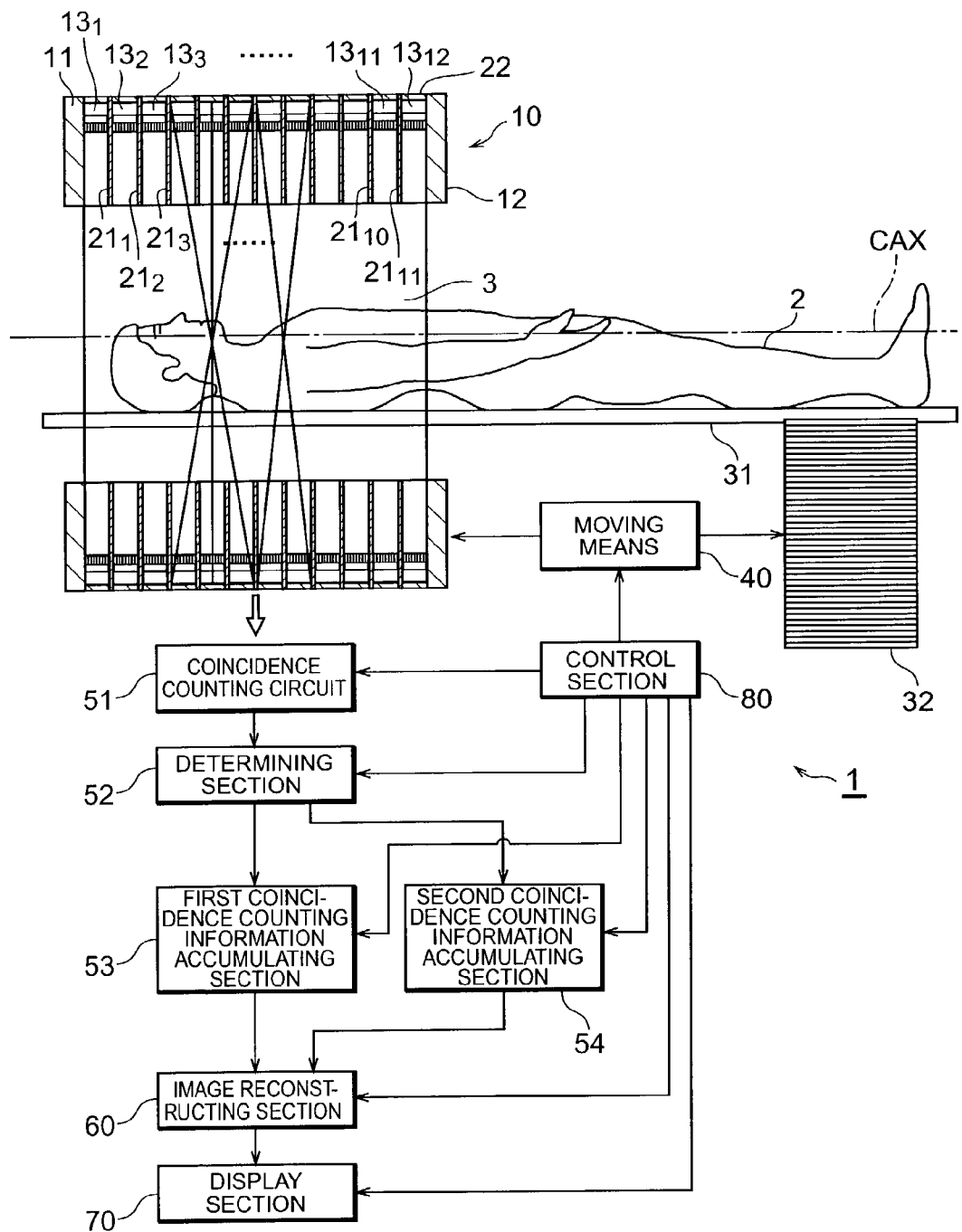
FIG. 1 is a schematic view showing the overall arrangement of a PET apparatus according to the embodiment.

An embodiment of the present invention will be described in detail below with reference to the accompanying drawings. Note that the same reference numerals denote the same elements throughout the drawings, and a repetitive description will be avoided. Note that a PET apparatus 1 according to this embodiment to be described below incorporates all the elements and steps defined in the appended claims.

The arrangement of the PET apparatus 1 according to this embodiment will be described first with reference to FIGS. 1 to 5. FIG. 1 is a view showing the schematic arrangement of the PET apparatus 1 according to this embodiment. FIG. 1 shows cross-sections of a detecting section 10 and slice collimators 21 taken along a plane including a central axis CAX. The PET apparatus 1 according to the embodiment includes the detecting section 10, slice collimators $21_1$ to $21_{11}$, a bed 31, a support base 32, a moving means 40, a coincidence counting circuit 51, a determining section 52, a first coincidence counting information accumulating section 53, a second coincidence counting information accumulating section 54, an image reconstructing section 60, and a display section 70. FIG. 1 also shows an object 2 to be examined which is an examination target for the PET apparatus 1. In addition, a space where the coincidence counting information of photon pairs can be detected by the PET apparatus 1 is shown as a measurement space 3.

The detecting section 10 has cylindrical detectors $13_1$ to $13_{12}$ arranged in a direction parallel to the central axis CAX between ring-like shield collimators 11 and 12. Each cylindrical detector $13_n$ is designed such that a plurality of photon detectors 15a for respectively detecting photons flying from the measurement space 3 including the central axis CAX are two-dimensionally arranged on a cylinder surrounding the central axis CAX. That is, each cylindrical detector $13_n$ is equivalent to a unit formed by stacking a plurality of detector rings, each formed by arranging a plurality of photon detectors 15a in form of a ring on a plane perpendicular to the central axis CAX, in a direction parallel to the central axis CAX. The slice collimators $21_1$ to $21_{11}$ are alternately arranged on the cylindrical detectors $13_1$ to $13_{12}$ in a direction parallel to the central axis CAX at least between the measurement space 3 and the detecting section 10 to pass only photons, of the photons flying from the measurement space 3, which are substantially parallel to a predetermined plane toward the detecting section 10. The detecting section 10 and slice collimators $21_1$ to $21_{11}$ will be described in detail later.

The bed 31 is used to place the object 2 thereon, and supported by the support base 32. The moving means 40 moves the detecting section 10 and slice collimators $21_1$ to $21_{11}$ together relative to the object 2 placed in the measurement space 3 in a direction parallel to the central axis CAX. More specifically, the moving means 40 may move the detecting section 10 and slice collimators $21_1$ to $21_{11}$ together in a direction parallel to the central axis CAX or may move the bed 31 (i.e., the object 2) in a direction parallel to the central axis CAX. In addition, the moving means 40 may move them in only one direction during measurement or reciprocate them. Relative movement is done by the moving means 40 such that the region of interest of the object 2 is moved by a distance equal to or more than ½ the arrangement pitch of the respective cylindrical detectors $13_n$ during measurement. Preferably, the region of interest of the object 2 is relatively moved at a constant speed in the measurement space 3 by a distance corresponding to an integer multiple of the above pitch during measurement. If the regions of interest of the object 2 exist over a predetermined range in the central axis CAX direction, it is preferable that each region in the predetermined range stay in the measurement space 3 for an almost constant period of time during measurement.

The first coincidence counting information accumulating section 53 and second coincidence counting information accumulating section 54 accumulate coincidence counting information of photon pairs detected by one pair of photon detectors 15a included in the detecting section 10 during a period in which the detecting section 10 and slice collimators $21_1$ to $21_{11}$ are moved relative to the object 2 by the moving means 40. When one pair of photon detectors 15a included in the detecting section 10 simultaneously detect a photon pair, the coincidence counting circuit 51 outputs position information indicating the position of each of the pair of photon detectors 15a.

The determining section 52 determines, on the basis of the position information output from the coincidence counting circuit 51, whether a straight line connecting light-receiving surfaces 15b of the pair of photon detectors 15a which simultaneously detected the photon pair crosses any one of the slice collimators $21_1$ to $21_{11}$. The determining section 52 may determine this by the calculation based on the geometrical structures of each cylindrical detector $13_n$ and each slice collimator $21_n$, or may determine this on the basis of the coincidence counting information obtained by rotating a rod-like calibration radiation source without placing the object 2 in the measurement space 3. In the latter case, the blank data obtained by blank measurement can be used, which is done to correct the sensitivity of the photon detector 15a.

It is also preferable that a calculation or measurement like that described above be performed in advance to determine whether a straight line connecting the light-receiving surfaces 15b of each pair of photon detectors 15a included in the detecting section 10 crosses any one of the slice collimators $21_n$, and information indicating whether the straight line crosses any one of the slice collimator $21_n$ be stored as data "1" or "0" in the form of a table in a ROM, a RAM, or the like. The determining section 52 reads out data from the table by using the position information output from the coincidence counting circuit 51 as an address, and determines, on the basis of this read data, whether the straight line connecting the light-receiving surfaces 15b of the pair of the photon detectors 15a which have simultaneously detected the photon pair crosses any one of the slice collimators $21_1$ to $21_{11}$.

When the determining section 52 determines that the above straight line crosses none of the slice collimators $21_1$ to $21_{11}$, the first coincidence counting information accumulating section 53 accumulates the coincidence counting information of the photon pair detected by the pair of photon detectors 15a. The coincidence counting information accumulated in the first coincidence counting information accumulating section 53 therefore includes true coincidence counting information obtained when photons are detected without being scattered and coincidence counting information obtained when scattered photons are detected. The coincidence counting information accumulated in the first coincidence counting information accumulating section 53 during measurement will be referred to as a signal sinogram S1.

When the determining section 52 determines that the above straight line crosses any one of the slice collimators $21_1$ to $21_{11}$, the second coincidence counting information accumulating section 54 accumulates the coincidence counting information of the photon pair detected by the pair of photon detectors 15a. The coincidence counting information accumulated in the second coincidence counting information accumulating section 54 therefore includes no true coincidence counting information obtained when photons are detected without being scattered, but includes only the coincidence counting information obtained when scattered photons are detected. The coincidence counting information accumulated in the second coincidence counting information accumulating section 54 during measurement will be referred to as a scatter sinogram S2.

In accumulating coincidence counting information in the first coincidence counting information accumulating section 53 and second coincidence counting information accumulating section 54, the coincidence counting information detected by the detecting section 10 is converted into information in a coordinate system fixed to the object 2 on the basis of the displacement amounts of the slice collimators $21_1$ to $21_{11}$ and detecting section 10 relative to the object 2, and the coincidence counting information having undergone this coordinate conversion is accumulated. Note that as the relative displacement amounts, the data obtained by an encoder or the like or the data recorded by the moving means 40 may be used.

The light-receiving surface 15b of each photon detector 15a included in the detecting section 10 has a predetermined area. Depending on the positions on the light-receiving surfaces 15b of one pair of photon detectors 15a which are connected by a straight line, the straight line may cross or may not cross any one of the slice collimators $21_1$ to $21_{11}$. In this case, the coincidence counting information detected by the pair of photon detectors 15a has an intermediate characteristic between the characteristic of the information accumulated as the signal sinogram S1 and the characteristic of the information accumulated as the scatter sinogram S2. It is therefore preferable that such information be accumulated in one of the first coincidence counting information accumulating section 53 and second coincidence counting information accumulating section 54 or discarded depending on the degree of this tendency.

The image reconstructing section 60 corrects the influence of scattered components in the coincidence counting information (signal sinogram S1) accumulated in the first coincidence counting information accumulating section 53 on the basis of the coincidence counting information (scatter sinogram S2) accumulated in the second coincidence counting information accumulating section 54, and reconstructs an image representing the spatial distribution of occurrence frequencies of photon pairs in the measurement space 3 on the basis of the corrected signal sinogram S1. This image reconstruction processing will be described in detail later.

The image reconstructing section 60 also performs sensitivity correction to correct variations in detection sensitivity of the respective photon detectors 15a of the detecting section 10 and absorption correction to correct the absorption of photons in the object 2. The display section 70 displays the reconstructed image obtained by the image reconstructing section 60. A control section 80 controls relative movement done by the moving means 40, outputting of the position information of a pair of photon detectors 15a by the coincidence counting circuit 51, determination done by the determining section 52, accumulation of coincidence counting information by the first coincidence counting information accumulating section 53, accumulation of coincidence counting information by the second coincidence counting information accumulating section 54, image reconstruction done by the image reconstructing section 60, and display of a reconstructed image by the display section 70.

Figure 2:
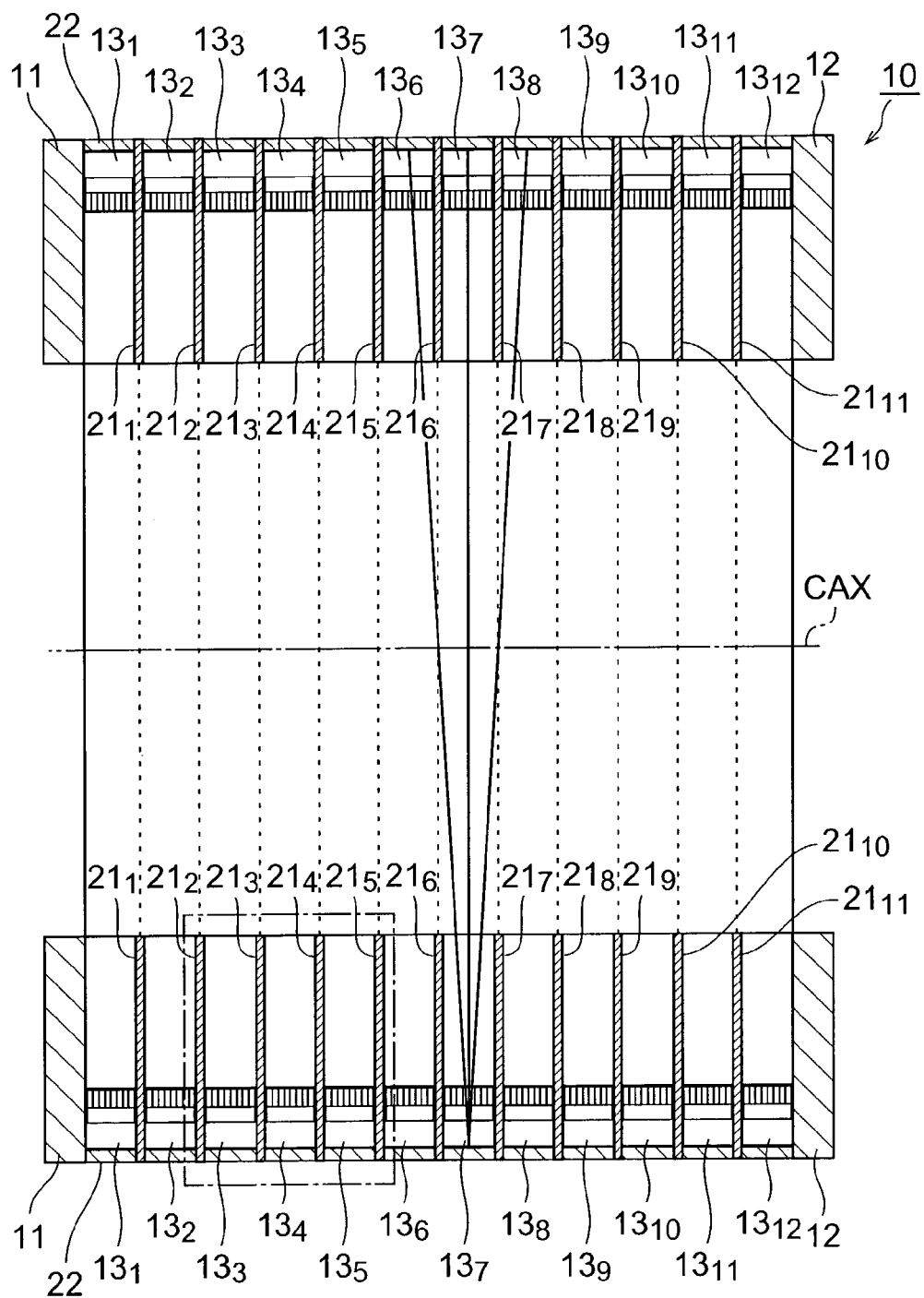
FIG. 2 is a view for explaining the arrangement of the detecting section and slice collimator of the PET apparatus according to this embodiment.

FIG. 2 is a view for explaining the arrangements of the detecting section 10 and slice collimator 21 of the PET apparatus according to this embodiment. FIG. 2 shows cross-sections of the detecting section 10 and slice collimators $21_1$ to $21_{11}$ taken along a plane including the central axis CAX. The detecting section 10 of the PET apparatus according to this embodiment includes the cylindrical detectors $13_1$ to $13_{12}$ stacked in a direction parallel to the central axis CAX between the ring-like shield collimators 11 and 12. The respective ring-like slice collimators $21_1$ to $21_{11}$ are located at least between the measurement space and the detecting section 10 and alternately arranged on the cylindrical detectors $13_n$ in a direction parallel to the central axis CAX. That is, each slice collimator $21_n$ is placed between the cylindrical detector $13_n$ and a cylindrical detector $13_{n+1}$ which are adjacent to each other. Each slice collimator $21_n$ is made of a material having a larger atomic number and larger specific gravity (e.g., lead or tungsten) and several mm (e.g., 5 mm to 6 mm) thick. Each slice collimator $21_n$ has a collimating function of passing photons, of photons flying from the measurement space, which are substantially parallel to a plane perpendicular to the central axis CAX toward the detecting section 10 and shielding obliquely incident photons.

Figure 3:
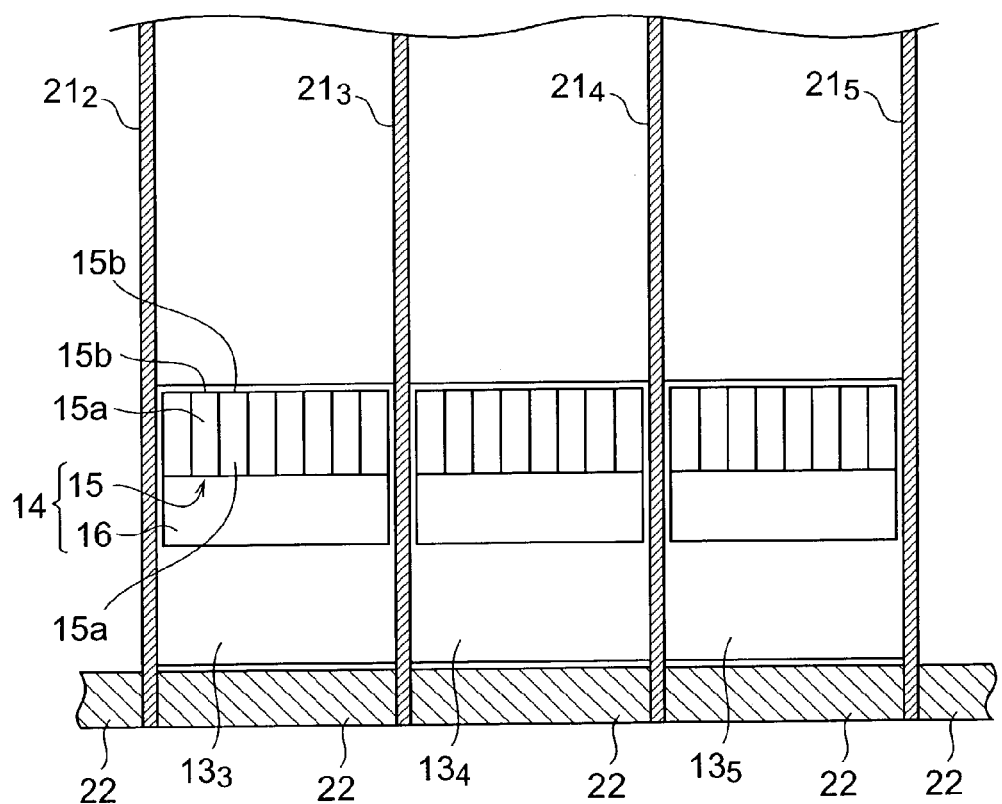
FIG. 3 is an enlarged view partly showing the detecting section and slice collimator of the PET apparatus according to this embodiment.
Figure 4:
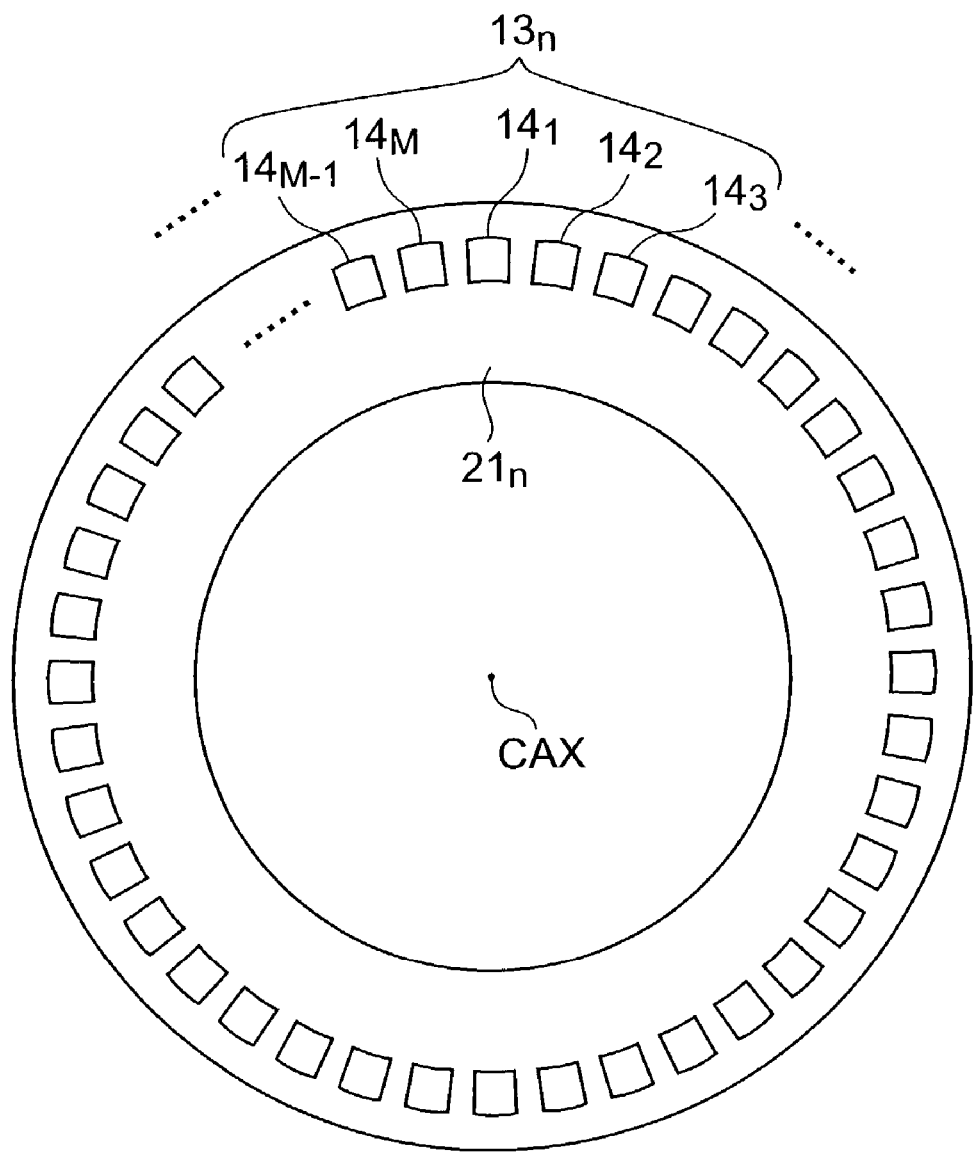
FIG. 4 is a view for explaining the arrangement of cylindrical detectors and slice collimators of the PET apparatus according to this embodiment.

FIG. 3 is an enlarged view of a portion (the portion enclosed with the chain line in FIG. 2) of the detecting section 10 and slice collimators 21 of the PET apparatus according to this embodiment. FIG. 4 is a view for explaining the arrangement of the cylindrical detector $13_n$ and slice collimator $21_n$ of the PET apparatus according to this embodiment. FIG. 4 shows the relationship between the cylindrical detector $13_n$ and the slice collimator $21_n$ when viewed from a direction parallel to the central axis CAX. Each cylindrical detector $13_n$ has a plurality of block detectors $41_1$ to $14_M$ arranged in the form of a ring on the same circumference on a plane perpendicular to the central axis CAX. Each block detector $14_m$ serves as a two-dimensional position detector for detecting the two-dimensional incident position of a photon incident on the light-receiving surface 15b. Each slice collimator $21_n$ reaches the rear portion of the corresponding cylindrical detector $13_n$ through the space between the cylindrical detector $13_n$ and the cylindrical detector $13_{n+1}$ which are adjacent to each other and is integrally fixed to a holding plate 22 at the rear portion.

Figure 5:
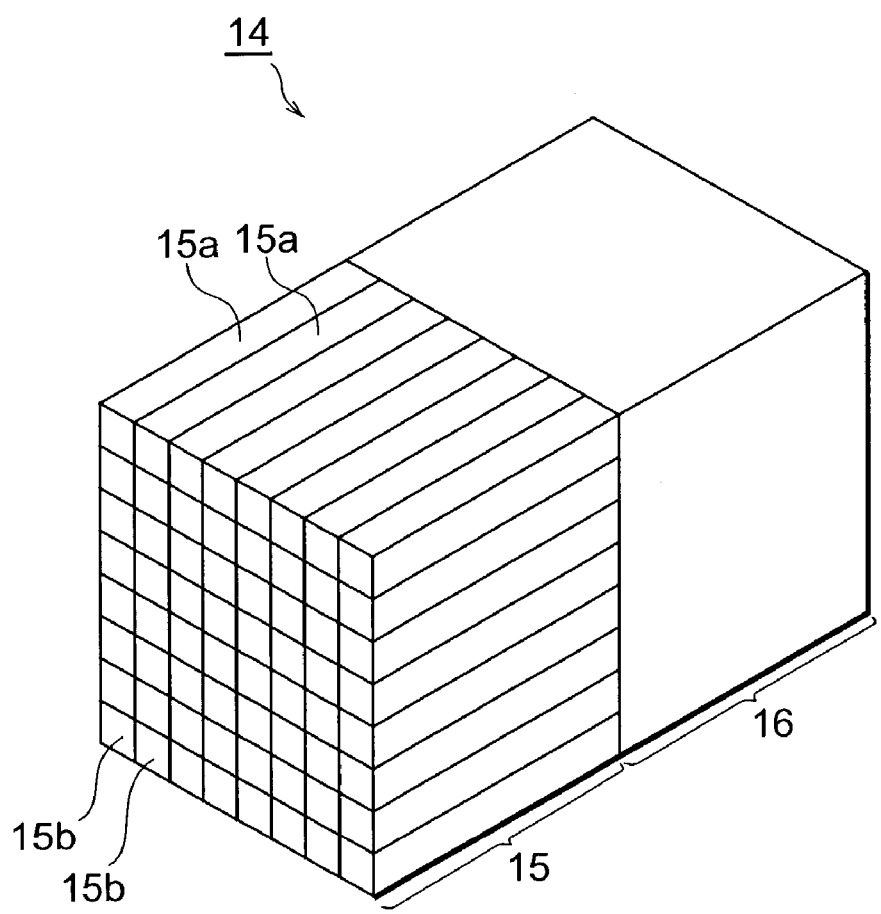
FIG. 5 is a view showing the arrangement of a block detector mounted in the PET apparatus according to this embodiment.

FIG. 5 is a view showing the arrangement of a block detector 14. As shown in FIG. 5, each block detector $14_m$ is a scintillation detector formed from a combination of a scintillation block 15 constituted by P×Q ($P \geq 2$, $Q \geq 2$) segments, and a position detection type photomultiplier 16.

Each block detector $14_m$ detects a photon flying from the measurement space and also detects the two-dimensional incident position of the photon incident on the light-receiving surface 15b of the scintillation block 15. That is, the block detector $14_m$ is equivalent to a unit obtained by two-dimensionally arranging P×Q small photon detectors 15a. Each cylindrical detector $13_n$ constituted by such block detectors $14_m$ arranged in the form of a ring is equivalent to a unit obtained by stacking a plurality of detector rings, each constituted by a plurality of photon detectors 15a arranged in the form of a ring on a plane perpendicular to the central axis CAX, in a direction parallel to the central axis CAX. In the block detector $14_m$, a resistor array for applying a predetermined voltage to each electrode in the position detection type photomultiplier 16 and a preamplifier for receiving the current signal output from the anode electrode of the position detection type photomultiplier 16 and outputting it as a voltage signal are housed in a casing, together with the scintillation block 15 and position detection type photomultiplier 16, for light shielding.

For example, BGO ($Bi_4Ge_3O_{12}$), GSO ($Gd_2SiO_5(Ce)$), LSO ($Lu_2SiO_5(Ce)$), or PWO ($PbWO_4$) is used for the scintillation block 15, as needed. The scintillation block 15 is constituted by 8×8 segments, and each segment has a size of 6 mm×6 mm×20 mm. The area of the photoelectric surface of the position detection type photomultiplier 16 is 50 mm×50 mm. The cylindrical detector $13_n$ is formed by arranging 60 block detectors $14_m$, each including the scintillation block 15 and position detection type photomultiplier 16, in the form of a ring. Each cylindrical detector $13_n$ has an inner diameter of about 1,000 mm. Each slice collimator $21_n$ has an inner diameter of 600 mm. The structure formed by alternately stacking the cylindrical detectors $13_1$ to $13_{12}$ and slice collimators $21_1$ to $21_{11}$ in a direction parallel to the central axis CAX has a thickness (i.e., the visual field in the body axis direction) of about 670 mm.

Under such conditions, detection of a pair of 511 keV photons (gamma rays) generated upon electron-positron pair annihilation in the measurement space 3 and flying in opposite directions, i.e., detection of coincidence counting information, may be performed by a pair of block detectors 14 in the same cylindrical detector $13_n$ or a pair of block detectors 14 respectively included in the adjacent cylindrical detectors $13_n$ and $13_{n+1}$. Detection of coincidence counting information may be performed by a pair of block detectors 14 included in two separate cylindrical detectors 13. In other words, detection of coincidence counting information may be performed between two adjacent detector rings or two separate detector rings as well as within the single detector ring.

That is, the PET apparatus 1 according to this embodiment has an intermediate arrangement between a conventional two-dimensional PET apparatus and a conventional three-dimensional PET apparatus. When sensitivity per unit visual field length (cm) in the body axis direction under the above conditions is calculated, the sensitivity of the PET apparatus 1 according to this embodiment is about 1.3 kcps/(kBq·ml), which is about ½ the sensitivity (about 2.58 kcps/(kBq·ml)) of the conventional three-dimensional PET apparatus, but is about four to five times higher than the sensitivity (about 0.28 kcps/(kBq·ml)) of the conventional two-dimensional PET apparatus.

Figure 6:
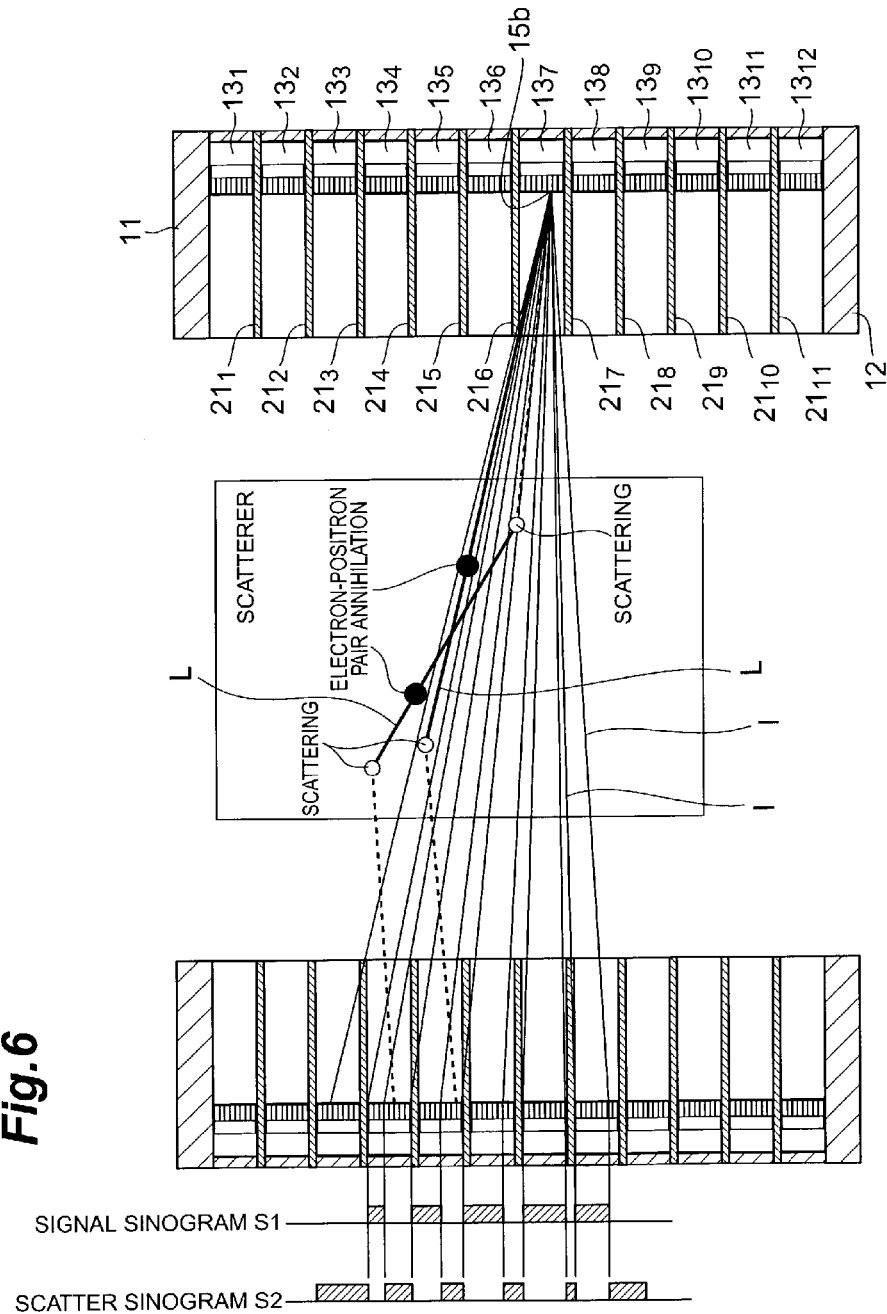
FIG. 6 is a view for explaining a signal sinogram S1 and scatter sinogram S2 in the PET apparatus according to this embodiment.

Each of the coincidence counting circuit 51, determining section 52, first coincidence counting information accumulating section 53, and second coincidence counting information accumulating section 54 will be described in further detail next with reference to FIGS. 6 to 9. FIG. 6 is a view for explaining the signal sinogram S1 and scatter sinogram S2. Referring to FIG. 6, thin solid lines 1 are coincidence counting lines extending from the light-receiving surface 15b of a given one of the photon detectors 15a as one end, and represent lines indicating the boundaries between coincidence counting information accumulated as the signal sinogram S1 and coincidence counting information accumulated as the scatter sinogram S2. The black bullets represent the positions of electron-positron pair annihilations. Thick solid lines L represent the flight paths of photons (gamma rays) generated upon electron-positron pair annihilations. The white bullets represent the positions where photons are scattered. The broken lines represent the flight paths of scattered photons.

As shown in FIG. 6, the coincidence counting information of scattered photons may be detected by one pair of photon detectors 15a whose coincidence counting line crosses one of the slice collimators $21_1$ to $21_{11}$. In such a case, the corresponding information is determined by the determining section 52, and the coincidence counting information is accumulated in the second coincidence counting information accumulating section 54, thereby generating the scatter sinogram S2. In addition, the coincidence counting information of scattered photons may also be detected, together with the true coincidence counting information of unscattered photons, by one pair of photon detector 15a whose coincidence counting line crosses none of the slice collimators $21_1$ to $21_{11}$. In this case, the corresponding information is determined by the determining section 52, and the coincidence counting information is accumulated by the first coincidence counting information accumulating section 53, thereby generating the signal sinogram S1.

Figure 7:
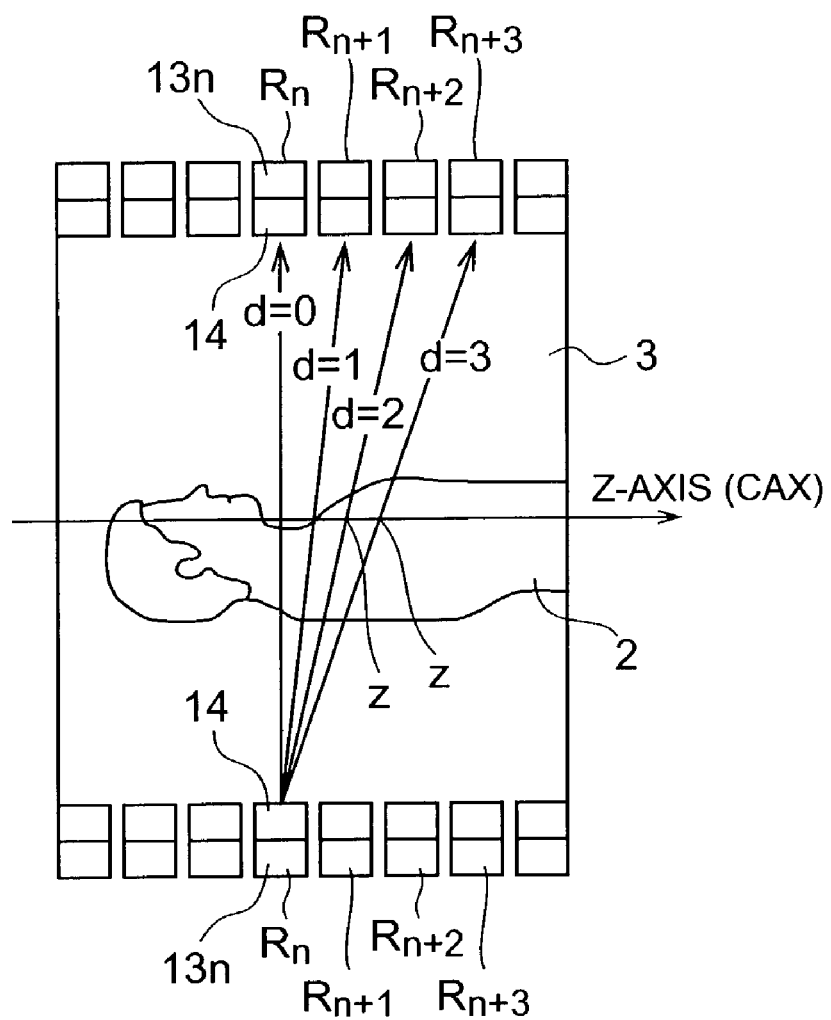
FIG. 7 is a view for explaining coincidence counting on a cross-section taken along a plane including the central axis (Z-axis) of the detecting section mounted in the PET apparatus according to this embodiment.

FIG. 7 is a view for explaining coincidence counting at a cross-section taken along a plane including the central axis CAX (Z-axis). Note that the illustration of the slice collimator $21_n$ is omitted in FIG. 7. Referring to FIG. 7, the four thick straight lines with arrows indicate planes (to be referred to as "projection planes" hereinafter) on which coincidence counting information is detected within a single detector ring or between two detector rings, including a projection plane (detector ring difference d=0) on which coincidence counting is done within the single detector ring $R_n$, a projection plane (detector ring difference d=1) on which coincidence counting is done between the two detector rings $R_n$ and $R_{n+1}$, a projection plane (detector ring difference d=2) on which coincidence counting is done between the two detector rings $R_n$ and $R_{n+2}$, and a projection plane (detector ring difference d=3) on which coincidence counting is done between the two detector rings $R_n$ and $R_{n+3}$. Note that the Z-coordinate of the point of intersection between each projection plane and the Z-axis is represented by z.

Figure 8:
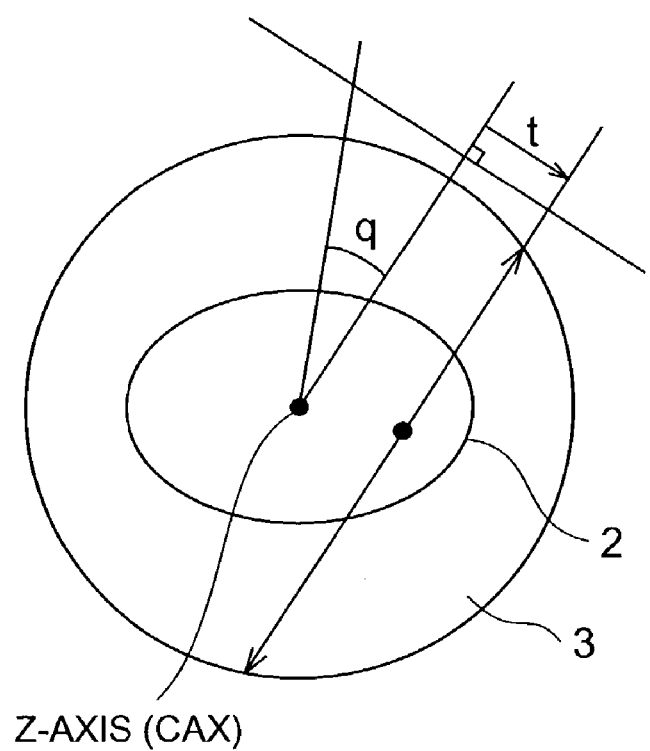
FIG. 8 is a view for explaining a coincidence counting line when viewed from a direction parallel to the central axis (Z-axis) of the detecting section mounted in the PET apparatus according to this embodiment.

FIG. 8 is a view for explaining a coincidence counting line, on one of the above projection planes, viewed from a direction parallel to the central axis CAX (Z-axis). Referring to FIG. 8, the line having arrows on its two ends represents a coincidence counting line; q, the azimuth angle in the direction in which coincidence counting is performed; and t, the position coordinate in a direction perpendicular to the direction in which coincidence counting is performed.

As shown in FIGS. 7 and 8, the coincidence counting line is specified by the distance t from the Z-axis on the projection plane, the azimuth angle q (=0 to 360°) viewed from a direction parallel to the Z-axis, the Z-axis coordinate value z at which the projection plane crosses the Z-axis, and the detector ring difference d (=0, 1, 2, 3, ...) When, therefore, one pair of photon detectors 15a included in the detecting section 10 simultaneously detect a pair of photons, the coincidence counting circuit 51 outputs the values of the four parameters t, q, z, and d as position information representing the position of each of the pair of photon detectors 15a. The determining section 52 determines, on the basis of the values of the four parameters t, q, z, and d output from the coincidence counting circuit 51, whether a straight line connecting the light-receiving surfaces 15b of the pair of photon detector 15a which have simultaneously detected the pair of photons crosses any one of the slice collimators $21_1$ to $21_{11}$.

Figure 9:
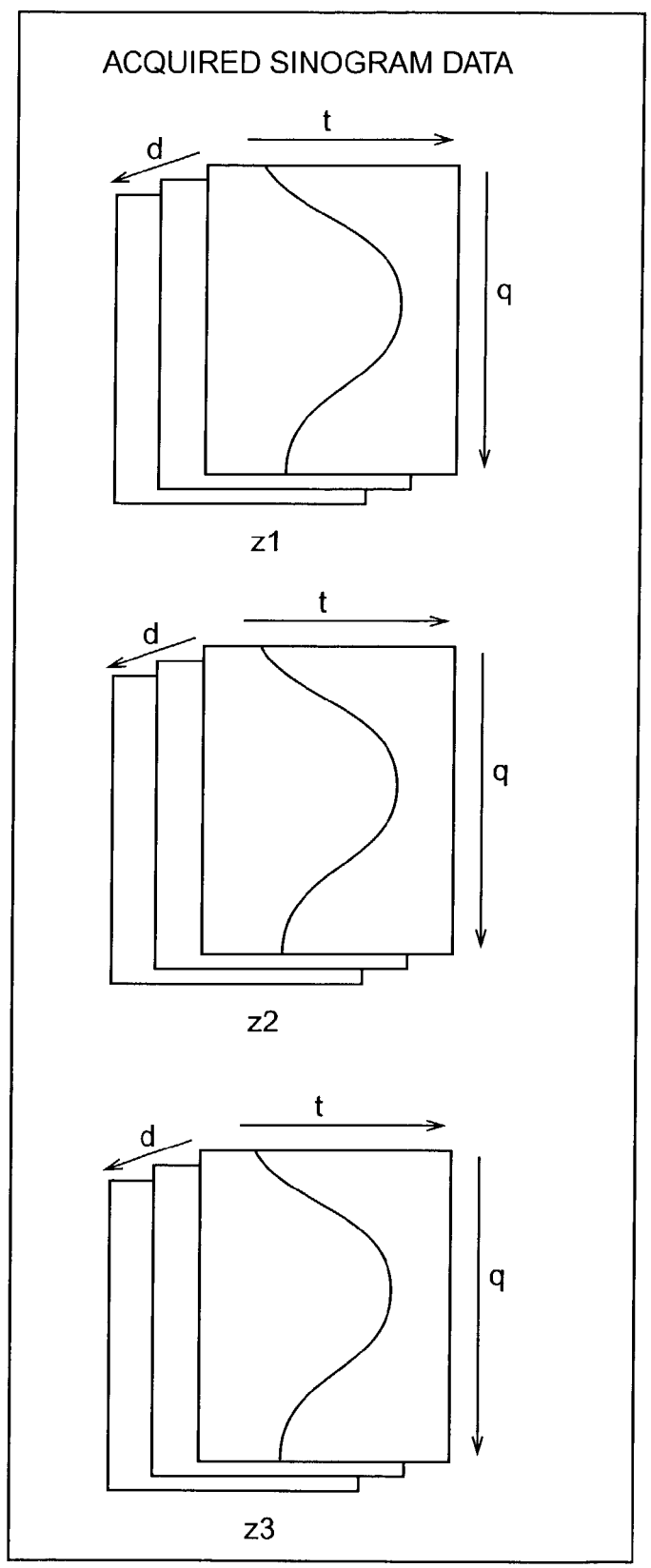
FIG. 9 is a view for explaining accumulation of coincidence counting information in the PET apparatus according to this embodiment.

FIG. 9 is a view for explaining accumulation of coincidence counting information. As shown in FIG. 9, the first coincidence counting information accumulating section 53 accumulates coincidence counting information with respect to each of the values of the four parameters t, q, z, and d to generate the signal sinogram S1(t, q, z, d). Likewise, the second coincidence counting information accumulating section 54 accumulates coincidence counting information with respect to each of the values of the four parameters t, q, z, and d to generate the scatter sinogram S2(t, q, z, d). In accumulating coincidence counting information in each of the first and second coincidence counting information accumulating sections 53 and 54, the coincidence counting information expressed in a coordinate system fixed to the object 2 is accumulated.

Image reconstruction in the image reconstructing section 60 will be described in further detail next. Note that the value of the parameter z is a value in a coordinate system fixed to the object 2 in the following description. First of all, the image reconstructing section 60 acquires the signal sinogram S1(t, q, z, d) generated by the first coincidence counting information accumulating section 53 accumulating coincidence counting information, and also acquires the scatter sinogram S2(t, q, z, d) generated by the second coincidence counting information accumulating section 54 accumulating coincidence counting information.

This scatter sinogram S2(t, q, z, d) exhibits a small change with respect to the parameter d, and hence the image reconstructing section 60 adds the scatter sinograms S2(t, q, z, d) concerning the parameter d. The resultant sinogram is represented by S3(t, q, z, d) in the following description. When the second coincidence counting information accumulating section 54 is to accumulate coincidence counting information, the section may accumulate coincidence counting information concerning the respective values of the three parameters t, q, and z, while neglecting the parameter d, to generate the scatter sinogram S3(t, q, z).

In addition, since this scatter sinogram S3(t, q, z) is sufficiently smooth with respect to the parameters z and t, the image reconstructing section 60 preferably smoothen the scatter sinogram S3(t, q, z) with respect to the parameters z and t by using a low-pass filter (e.g., Gaussian function filter having a half-value width of about 5 cm). This can reduce statistical noise.

The image reconstructing section 60 then corrects the influence of scattered components on the signal sinogram S1(t, q, z, d) on the basis of the scatter sinogram S3(t, q, z) obtained in the above manner to obtain a true signal sinogram S(t, q, z, d). More specifically, the image reconstructing section 60 obtains the true signal sinogram S(t, q, z, d) by $$S(t,q,z,d)=S1(t,q,z,d)-k \cdot S3(t,q,z) \cdot K(d)$$

where K(d) is a sensitivity correction coefficient for correcting the sensitivity of photon detection by a pair of photon detectors 15a and a function of the parameter d which is obtained on the basis of the blank data obtained by the above-described blank measurement. The value of the constant k is so determined as to minimize the absolute value of the true signal sinogram S(t, q, z, d) outside the object 2.

Figure 10:
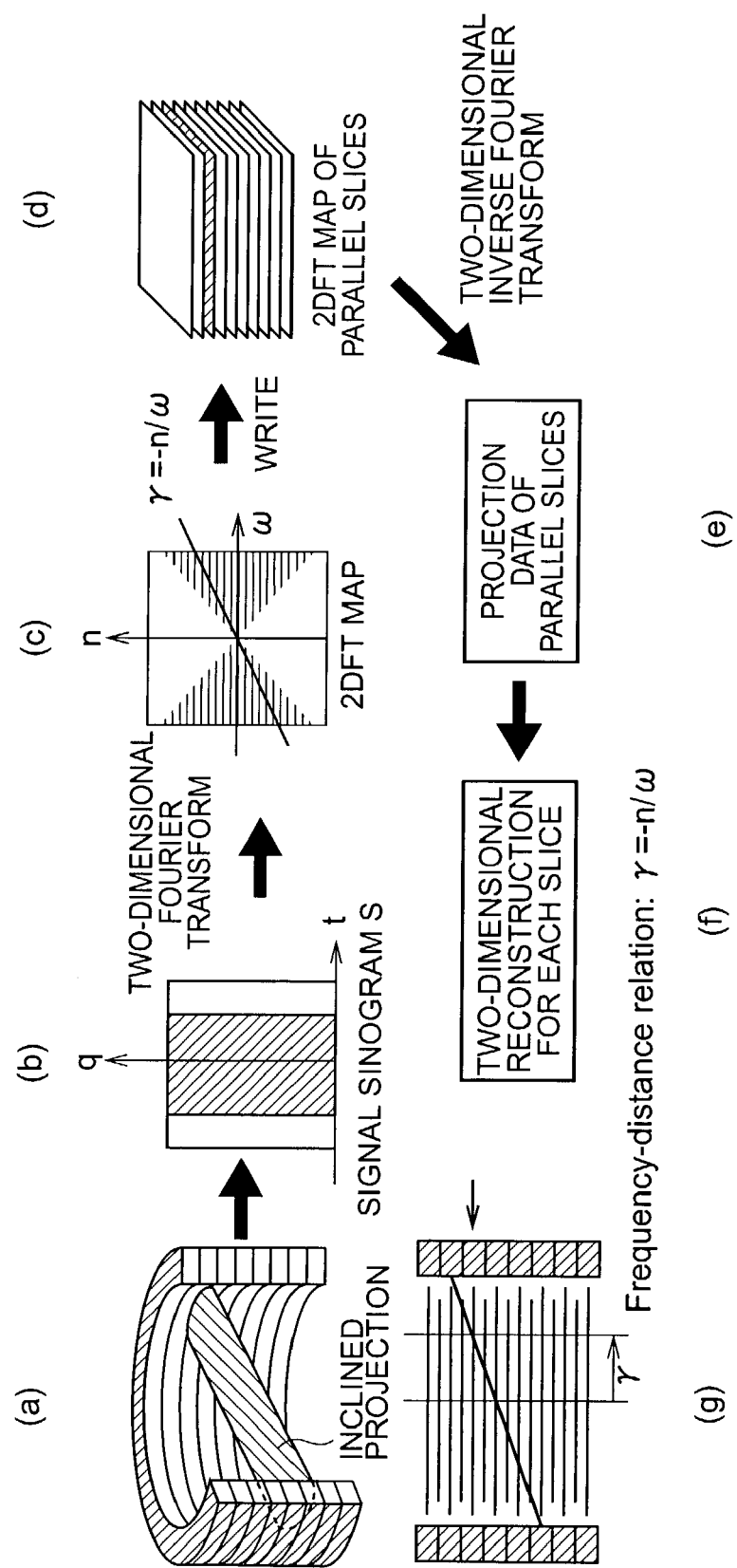
FIG. 10 is a view for explaining the Fourier Rebinning method in the PET apparatus according to this embodiment.
Figure 11:
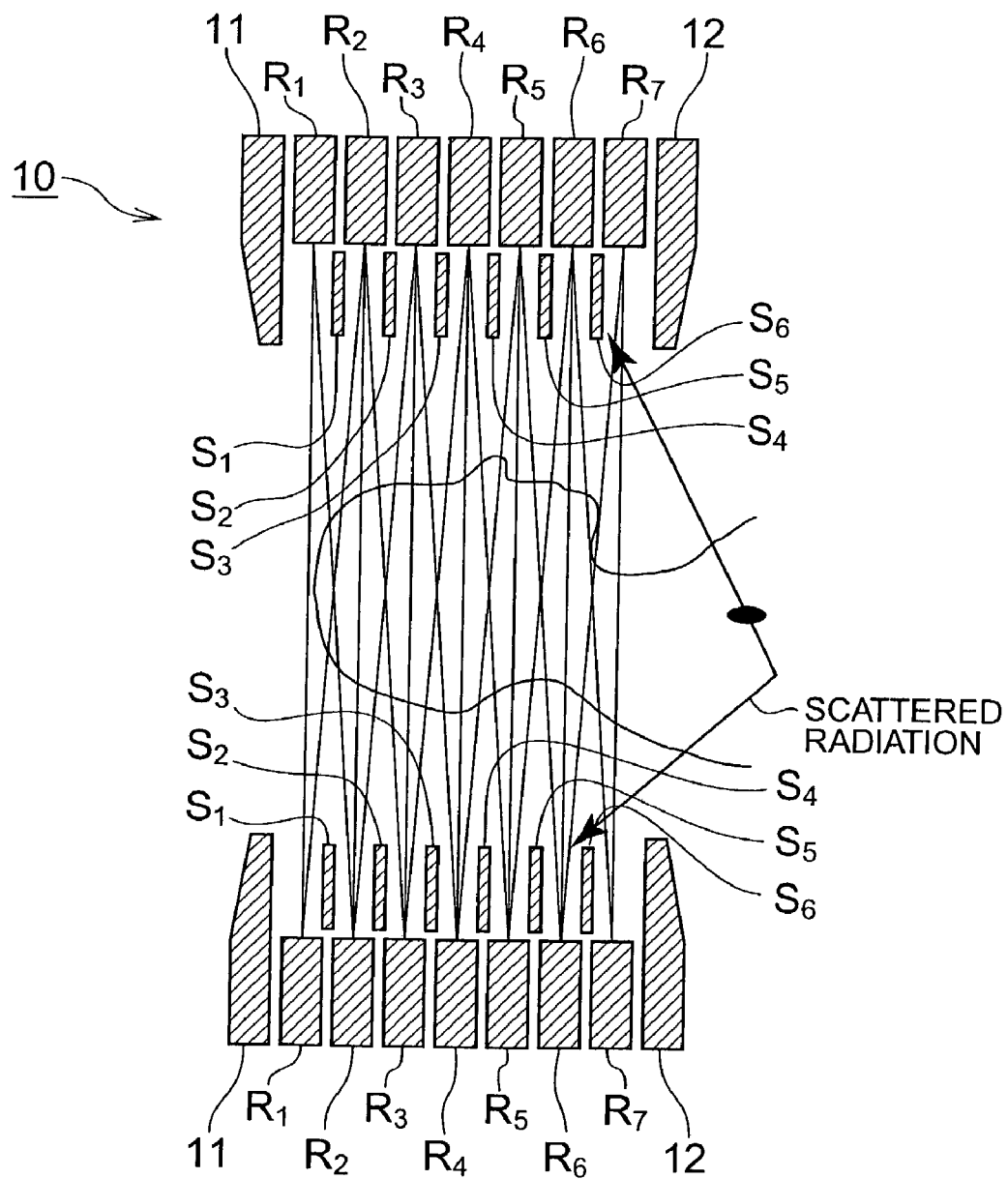
FIG. 11 is a view for explaining the arrangement of the detecting section of a two-dimensional PET apparatus.
Figure 12:
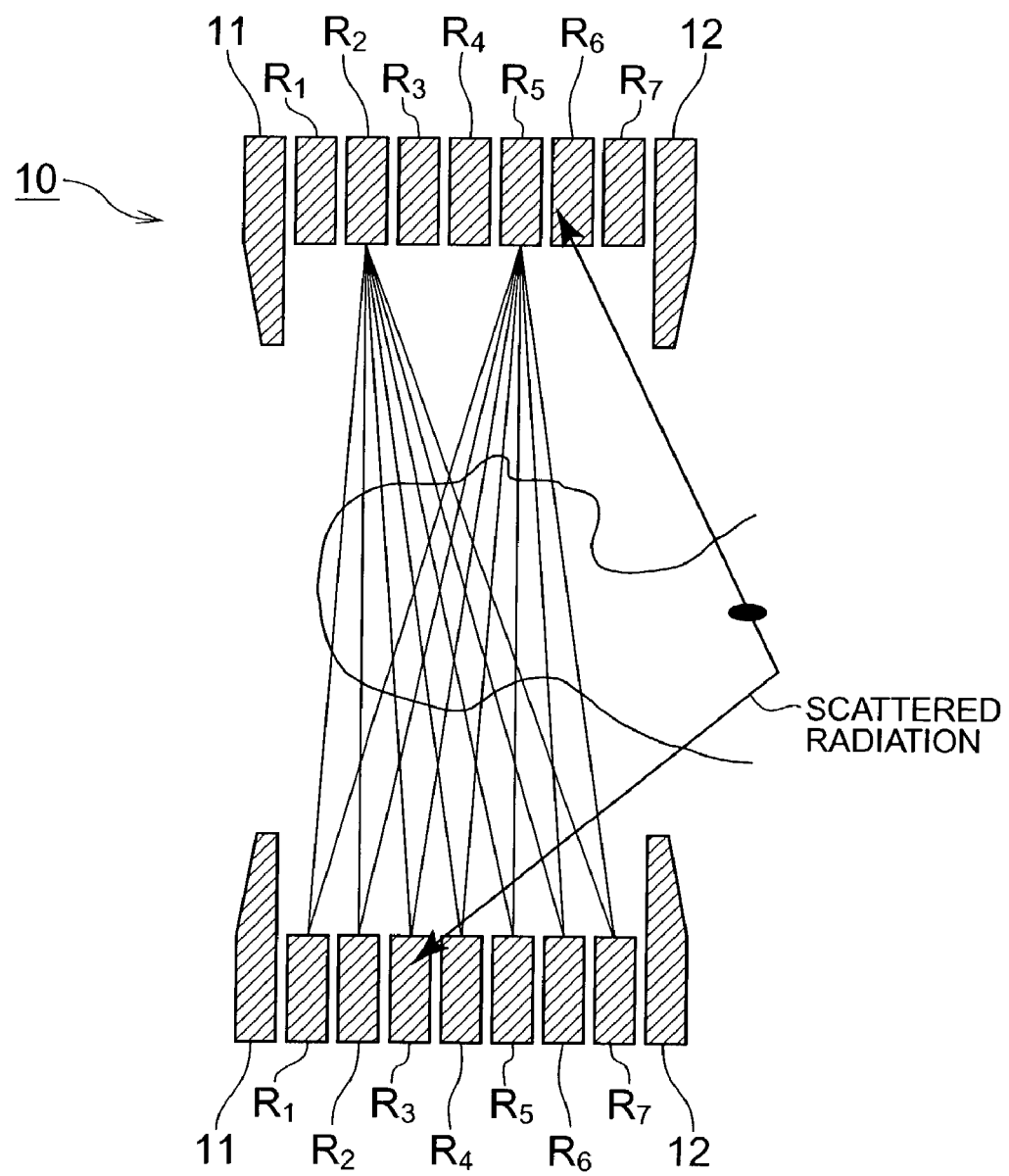
FIG. 12 is a view for explaining the arrangement of the detecting section of a three-dimensional PET apparatus.

Subsequently, the image reconstructing section 60 reconstructs an image representing the spatial distribution of occurrence frequencies of photon pairs in the measurement space 3 on the basis of the true signal sinogram S(t, q, z, d) obtained in the above manner. As an algorithm for this image reconstruction, a three-dimensional filter inverse projection method or Fourier Rebinning method is used, as needed. The three-dimensional filter inverse projection method is theoretically a three-dimensional extended version of the two-dimensional filter inverse projection method widely used in X-ray CT and the like. This is a method of obtaining a reconstructed image by applying appropriate two-dimensional filtering to two-dimensional projection data measured in various projecting directions and then performing three-dimensional inverse projection of them in the respective directions. In the Fourier Rebinning method, as shown in FIG. 10, the true signal sinogram S ("(b)" in FIG. 10) corresponding to an inclined projection ("(a)" in FIG. 10) on the detector ring surface is subjected to two-dimensional Fourier transform with respect to the parameters t and q to obtain a two-dimensional Fourier transform map ("(c)" in FIG. 10) with respect to variables n and ω. This two-dimensional Fourier transform map is transformed into two-dimensional Fourier transform maps ("(d)" in FIG. 10) of slices parallel to the detector ring surface by using "Frequency-distance relation", i.e., "γ=−n/ω". Each parallel slice two-dimensional Fourier transform map obtained in this manner is subjected to two-dimensional inverse Fourier transform to obtain projection data of each parallel slice ("(e)" in FIG. 10). A reconstructed image ("(f)" in FIG. 10) is obtained by performing two-dimensional image reconstruction with respect to the projection data of each parallel slice.

An image generating method in the PET apparatus 1 according to this embodiment will be described next. The object 2 to which an RI is applied is placed on the bed 31, and the region of interest of the object 2 is positioned in the measurement space 3. The PET apparatus 1 operates in the following manner under the control of the control section 80. First of all, the moving means 40 starts to move the detecting section 10 and slice collimators $21_1$ to $21_{11}$ together relative to the object 2 placed in the measurement space 3 in a direction parallel to the central axis CAX.

Of the 511 keV photons (gamma rays) generated upon electron-positron pair annihilation in the measurement space 3, photons that have reached the detecting section 10 without being shielded by the slice collimators $21_1$ to $21_{11}$ are simultaneously detected by one pair of photon detectors 15a included in the detecting section 10, and position information indicating the position of each of the pair of photon detectors 15a is output from the coincidence counting circuit 51. The determining section 52 determines, on the basis of the position information output from the coincidence counting circuit 51, whether a straight line connecting the light-receiving surfaces 15b of the pair of photon detectors 15a which have simultaneously detected the photon pair crosses any one of the slice collimators $21_1$ to $21_{11}$.

If the determining section 52 determines that the straight line crosses none of the slice collimators $21_1$ to $21_{11}$, the coincidence counting information of the photon pair detected by the pair of photon detectors 15a is converted into information in a coordinate system fixed to the object 2. The resultant information is then accumulated in the first coincidence counting information accumulating section 53. If the determining section 52 determines that the straight line crosses one of the slice collimators $21_1$ to $21_{11}$, the coincidence counting information of the photon pair detected by the pair of photon detectors 15a is converted into information in the coordinate system fixed to the object 2. The resultant information is then accumulated in the second coincidence counting information accumulating section 54.

When a predetermined measurement period comes to an end, the first and second coincidence counting information accumulating sections 53 and 54 stop accumulating coincidence counting information, and the moving means 40 also stops relative movement. The image reconstructing section 60 corrects the influence of scattered components on the signal sinogram S1 accumulated and generated by the first coincidence counting information accumulating section 53 on the basis of the scatter sinogram S2 accumulated and generated by the second coincidence counting information accumulating section 54, and reconstructs an image representing the spatial distribution of occurrence frequencies of photon pairs in the measurement space 3 on the basis of the corrected signal sinogram S1. The image reconstructing section 60 also performs sensitivity correction and absorption correction. The reconstructed image obtained by the image reconstructing section 60 is displayed by the display section 70.

As described above, the detecting section 10 of the PET apparatus 1 according to this embodiment has the cylindrical detectors $13_1$ to $13_{12}$ arrayed in a direction parallel to the central axis CAX, and each cylindrical detector $13_n$ is formed by two-dimensionally arraying a plurality of photon detectors 15a on the cylinder surrounding the central axis CAX. The cylindrical detectors $13_1$ to $13_{12}$ and slice collimators $21_1$ to $21_{11}$ are alternately arranged in a direction parallel to the central axis CAX. With this arrangement of the detecting section 10, the resolution of a reconstructed image can be improved by reducing the size of each photon detector 15a. In addition, since the slice collimators $12_n$ are not arranged between the detector rings but are arranged between the cylindrical detectors $13_n$, intervals are ensured between the respective slice collimators $12_n$ to suppress a decrease in open area ratio, thus ensuring high photon pair detection sensitivity. In addition, since each slice collimator $12_n$ need not be thinned, the collimating effect can be maintained, and scattered radiation can be efficiently removed. This makes it possible to ensure high quantitativeness of a reconstructed image. As described above, the PET apparatus 1 according to this embodiment can ensure good photon pair detection sensitivity and quantitativeness while improving the resolution of a reconstructed image.

In addition, in this embodiment, the determining section 52 determines whether a straight line connecting the light-receiving surfaces 15b of one pair of photon detectors 15a which have simultaneously detected a photon pair crosses any one of the slice collimators $21_1$ to $21_{11}$, and the first coincidence counting information accumulating section 53 generates the signal sinogram S1 on the basis of this determination result. In addition, the second coincidence counting information accumulating section 54 generates the scatter sinogram S2 on the basis of the determination result. The image reconstructing section 60 then corrects the influence of scattered components on the signal sinogram S1 on the basis of the scatter sinogram S2, and reconstructs an image on the basis of the corrected signal sinogram S1. In this manner, this embodiment corrects the influence of scattered components on the signal sinogram S1 on the basis of the scatter sinogram S2 as well as removing scattered radiation by the slice collimators $21_1$ to $21_{11}$, and hence the quantitativeness of a reconstructed image is excellent.

The scatter correction method according to this embodiment has the following merits as compared with the conventional scatter correction methods. According to the first scatter correction method (energy window method), a signal sinogram is obtained by accumulating coincidence counting information of 511 keV photon pairs, and a scatter sinogram is obtained by accumulating photons with lower energy as components having undergone Compton scattering in an object to be examined. The product of the scatter sinogram and a given constant is then subtracted from the signal sinogram to obtain a true signal sinogram. The first scatter correction method is effective in removing scattered radiation from outside the visual field in the body axis direction, but requires photon detection elements to have excellent energy resolution characteristics. This method cannot therefore be applied to a case wherein photon detection elements including scintillators that emit only a small amount of light and exhibit low energy resolution are used. In contrast to this, the scatter correction method in this embodiment can be applied to a case wherein photon detection elements including scintillators that emit only a small amount of light and exhibit low energy resolution are used, because there is no need to perform energy analysis.

According to the second scatter correction method (a kind of calculation method), a scatter response is acquired in advance by placing a point radiation source in a uniform water phantom having a shape similar to that of an object to be examined, and a signal sinogram is acquired by placing the object and measuring it. A pseudo scatter sinogram is obtained by convolution integration of the signal sinogram and scatter response, and the scatter sinogram is subtracted from the signal sinogram, thereby obtaining a true signal sinogram. In the second scatter correction method, scattered components can be removed more accurately by repeating the above convolution integration and subtraction. The second scatter correction method is designed to perform correction based on a radiation source distribution existing in the visual field, and hence cannot remove scattered radiation from outside the visual field. In contrast to this, in the scatter correction method in this embodiment, since a scatter sinogram is directly obtained in a state wherein an object to be examined is placed in the measurement space, a signal sinogram can be accurately corrected by a simple calculation. In addition, scattered radiation from outside the visual field can be removed.

According to the third scatter correction method (another kind of calculation method), a scatter profile is approximately estimated by interpolating a scatter profile outside an object to be examined into the object in consideration of the fact that a portion of a signal sinogram which corresponds to a portion outside the object is constituted by only scattered components. A true signal sinogram is then obtained by subtracting the scattered profile from the signal sinogram. The third scatter correction method can approximate a scatter profile relatively accurately when a radiation source distribution inside the object is relatively uniform. If, however, radiation sources are localized in the object, the scatter profile may have a complicated shape, which is difficult to estimate. In contrast to this, in the scatter correction method in this embodiment, since a scatter sinogram is directly obtained while an object to be examined is placed in the measurement space, a signal sinogram can be accurately corrected by a simple calculation, and scattered radiation from outside the visual field can be removed.

As described above, in the PET apparatus 1 according to this embodiment, the detecting section 10 and slice collimators $21_1$ to $21_{11}$ are arranged in the above manner, and scatter correction is performed in the above manner on the basis of the signal sinogram S1 and scatter sinogram S2 simultaneously acquired during one measurement period. This makes it possible to ensure good photon pair detection sensitivity and quantitativeness while improving the resolution of a reconstructed image. In comparison with the conventional methods, the scatter correction method of this embodiment, in particular, can be applied to a case wherein the photon detectors 15a including scintillators that emit only a small amount of light and exhibit poor energy resolution are used, and can accurately correct a signal sinogram with a simple, quick calculation. In addition, scattered radiation from outside the visual field can advantageously be removed.

While the detecting section 10 and slice collimators $21_1$ to $21_{11}$ are moved together relative to the object 2 in a direction parallel to the central axis CAX by the moving means 40, coincidence counting information is accumulated by the first coincidence counting information accumulating section 53 or second coincidence counting information accumulating section 54, and a reconstructed image is obtained by the image reconstructing section 60 on the basis of this accumulated coincidence counting information (signal sinogram S1 and scatter sinogram S2). In this embodiment, therefore, even with the above arrangement of the cylindrical detectors $13_1$ to $13_{12}$ and slice collimators $21_1$ to $21_{11}$, photon pairs can be detected with uniform sensitivity in the body axis direction of the object 2, and the quantitativeness of a reconstructed image can be made uniform.

In addition, in this embodiment, each cylindrical detector $13_n$ is formed from a ring-like array of a plurality of two-dimensional detectors (block detectors $14_m$) which detect the two-dimensional incident positions of photons incident on the light-receiving surfaces 15b. This arrangement is therefore suitable to improve the resolution of a reconstructed image by reducing the size of each photon detector 15a.

In this embodiment, the slice collimator $21_n$ reaches the rear portion of each cylindrical detector $13_n$ through the space between the cylindrical detector $13_n$ and the cylindrical detector $13_{n+1}$, and is integrally fixed by the holding plate 22 at the rear portion. In this case, the precision of relative positional relationship between each cylindrical detector $13_n$ and a corresponding one of the slice collimators $21_n$ is high, and the respective cylindrical detectors $13_n$ and the respective slice collimators $21_n$ are alternately arranged in a direction parallel to the central axis CAX. This ensures high incidence efficiency of photons on each cylindrical detector $13_n$ and sufficiently high performance. In addition, since there is no need to strictly manage process accuracy and assembly accuracy for the respective cylindrical detectors $13_n$, slice collimators $21_n$, holding plate 22, and the like, the apparatus can be easily manufactured at low cost. Furthermore, this arrangement is suitable to move the detecting section 10 and slice collimators $21_1$ to $21_{11}$ together in a direction parallel to the central axis CAX.

INDUSTRIAL APPLICABILITY

As has been described in detail above, detection of coincidence counting information may be performed by a pair of photon detection elements in a single cylindrical detector included in the detecting section, or a pair of photon detection elements respectively included in two adjacent cylindrical detectors depending on the sizes of each cylindrical detector and each slice collimator, or a pair of photon detection elements included in two separate cylindrical detectors. In other words, detection of coincidence counting information may be performed between two adjacent detector rings or between two separate detector rings as well as within the single detector ring. That is, the PET apparatus according to the present invention has an intermediate arrangement between a conventional two-dimensional PET apparatus and a conventional three-dimensional PET apparatus, and has sensitivity about several times higher than that of the conventional two-dimensional PET apparatus. The PET apparatus according to the present invention can therefore ensure good photon pair detection sensitivity and quantitativeness while improving the resolution of a reconstructed image.

In the PET apparatus according to the present invention, in particular, the determining section determines whether a straight line connecting the light-receiving surfaces of a pair of photon detection elements which have simultaneously detected a photon pair crosses any one of the slice collimators. The first coincidence counting information accumulating section generates a signal sinogram on the basis of this determination result. The second coincidence counting information accumulating section generates a scatter sinogram. The image reconstructing section then corrects the influence of scattered components on the signal sinogram on the basis of the scatter sinogram, and reconstructs an image on the basis of the corrected signal sinogram. As described above, according to the present invention, scattered radiation is removed by a plurality of slice collimators, and the influence of scattered components on the signal sinogram is corrected on the basis of the scatter sinogram. This makes a reconstructed image have excellent quantitativeness.

The invention claimed is:

1. A PET apparatus comprising:
   a detecting section which includes a plurality of cylindrical detectors each formed by two-dimensionally arraying a plurality of photon detection elements, each of which detects a photon flying from a measurement space including a central axis, on a cylinder surrounding the central axis, the plurality of cylindrical detectors being arrayed in a direction parallel to the central axis;
   a plurality of slice collimators which are alternately arranged with said cylindrical detectors at least between the measurement space and said detecting section in a direction parallel to the central axis, and pass only photons, of photons flying from the measurement space, which are substantially parallel to a predetermined plane perpendicular to the central axis toward said detecting section;
   a determining section which determines, when a pair of photon detection elements included in said detecting section simultaneously detect a photon pair, whether a straight line connecting light-receiving surfaces of the pair of photon detection elements crosses any one of said plurality of slice collimators;
   a first coincidence counting information accumulating section which accumulates coincidence counting information of the photon pair detected by the pair of photon detection elements when said determining section determines that the straight line crosses none of said plurality of slice collimators;

a second coincidence counting information accumulating section which accumulates coincidence counting information of the photon pair detected by the pair of photon detection elements when said determining section determines that the straight line crosses one of said plurality of slice collimators; and an image reconstructing section which corrects an influence of a scattered component on the coincidence counting information accumulated by said first coincidence counting information accumulating section on the basis of the coincidence counting information accumulated by said second coincidence counting information accumulating section, and reconstructs an image representing a spatial distribution of occurrence frequencies of photon pairs in the measurement space on the basis of the corrected coincidence counting information.

2. A PET apparatus according to claim 1, wherein said cylindrical detector is formed by arraying a plurality of two-dimensional position detectors, each of which detects a two-dimensional position of a light-receiving surface when a photon is incident thereon, on the predetermined plane in the form of a ring.

3. A PET apparatus according to claim 1, wherein
said apparatus further comprises moving means for moving said detecting section and said plurality of slice collimators together relative to an object to be examined which is placed in the measurement space in a direction parallel to the central axis, and
said first and second coincidence counting information accumulating sections respectively acquire coincidence counting information during a period in which said detecting section and said plurality of slice collimators are moved relative to the object by said moving means, convert the coincidence counting information into information in a coordinate system fixed to the object, and accumulate the information.

4. A PET apparatus comprising:
a plurality of photon detection elements which are arranged around a measurement space and detect one photon and the other photon which are produced upon electron-positron pair annihilation;
a plurality of collimators which guide only the photon flying from a predetermined direction toward each of said plurality of photon detection elements;
a determining section which determines, when detection of said one photon by one of said plurality of photon detection elements and detection of said other photon by one of said plurality of photon detection elements are simultaneously done, whether a straight line connecting a light-receiving surface of said photon detection element which has detected said one photon and a light-receiving surface of said photon detection element which has detected said other photon crosses any one of said plurality of collimators;
a first coincidence counting information accumulating section which accumulates coincidence counting information of said one photon and said other photon when said determining section determines that the straight line crosses none of said plurality of slice collimators;
a second coincidence counting information accumulating section which accumulates coincidence counting information of said one photon and said other photon when said determining section determines that the straight line crosses one of said plurality of slice collimators; and an image reconstructing section which corrects an influence of a scattered component on the coincidence counting information accumulated by said first coincidence counting information accumulating section on the basis of the coincidence counting information accumulated by said second coincidence counting information accumulating section, and reconstructs an image representing a spatial distribution of occurrence frequencies of a pair of said one photon and said other photon in the measurement space on the basis of the corrected coincidence counting information.

5. A PET apparatus according to claim 4, wherein said plurality of photon detection elements are two-dimensionally arrayed to specify positions of the light-receiving surfaces of said photon detection elements which have detected said one photon and said other photon.

6. A PET apparatus according to claim 5, wherein
the measurement space has a cylindrical shape, and
said plurality of photon detection elements are two-dimensionally arrayed on a side surface of the cylindrical shape.

7. A PET apparatus according to claim 6, wherein
said plurality of photon detection elements are two-dimensionally arrayed to form a plurality of block detectors, and
said plurality of block detectors are arranged on a side surface of the cylindrical shape in the form of a ring to two-dimensionally array said plurality of photon detection elements on the side surface of the cylindrical shape.

8. A PET apparatus according to claim 4, further comprising means for, when said one photon and said other photon are simultaneously detected, outputting to said determining section position information indicating a position of said photon detection element which has detected said one photon and a position of said photon detection element which has detected said other photon.

9. A PET apparatus according to claim 4, further comprising means for displaying the image reconstructed by said image reconstructing section.

10. An image generating method for a PET apparatus including
a plurality of photon detection elements which are arranged around a measurement space and detect one photon and the other photon which are produced upon electron-positron pair annihilation, and
a plurality of collimators which guide only the photon flying from a predetermined direction toward each of the plurality of photon detection elements, comprising:
the determining step of determining, when detection of said one photon by one of the plurality of photon detection elements and detection of said other photon by one of the plurality of photon detection elements are simultaneously done, whether a straight line connecting a light-receiving surface of the photon detection element which has detected said one photon and a light-receiving surface of the photon detection element which has detected said other photon crosses any one of the plurality of collimators;
the first coincidence counting information accumulating step of accumulating coincidence counting information of said one photon and said other photon when it is determined in the determining step that that the straight line crosses none of the plurality of slice collimators;
the second coincidence counting information accumulating step of accumulating coincidence counting information of said one photon and said other photon when it is determined in the determining step that the straight line crosses one of the plurality of slice collimators; and the image reconstructing step of correcting an influence of a scattered component on the coincidence counting information accumulated in the first coincidence counting information accumulating step on the basis of the coincidence counting information accumulated in the second coincidence counting information accumulating step, and reconstructing an image representing a spatial distribution of occurrence frequencies of a pair of said one photon and said other photon in the measurement space on the basis of the corrected coincidence counting information.

11. An image generating method for a PET apparatus according to claim 10, wherein the method further comprises the step of, when said one photon and said other photon are simultaneously detected, outputting position information indicating a position of said photon detection element which has detected said one photon and a position of said photon detection element which has detected said other photon, and the determining step is performed on the basis of the position information.

12. An image generating method for a PET apparatus according to claim 10, further comprising the display step of displaying the image reconstructed in the image reconstructing step.

* * * * *